United States Patent [19]

McCarty

[11] Patent Number: 4,582,606
[45] Date of Patent: Apr. 15, 1986

[54] APPARATUS FOR SEPARATING OR COLLECTING DIFFERENT DENSITY LIQUID COMPONENTS

[75] Inventor: Read S. McCarty, Rockland, Mass.
[73] Assignee: Neotech, Inc., Rockland, Mass.
[21] Appl. No.: 574,889
[22] Filed: Jan. 30, 1984
[51] Int. Cl.$^4$ .............................................. B01D 21/26
[52] U.S. Cl. .................................... 210/516; 210/927; 494/21; 494/45
[58] Field of Search .......................... 494/16, 21, 45; 210/516, 927

[56] References Cited

U.S. PATENT DOCUMENTS

| | | | |
|---|---|---|---|
| 3,064,647 | 11/1962 | Earl | 494/21 X |
| 3,750,645 | 8/1973 | Bennett et al. | 210/787 X |
| 3,800,947 | 4/1974 | Smith | 210/927 X |
| 3,887,464 | 6/1975 | Ayres | 210/927 X |
| 3,935,113 | 1/1976 | Ayres | 210/927 X |
| 3,945,928 | 3/1976 | Ayres | 210/927 X |
| 4,187,861 | 2/1980 | Heffernan | 210/927 X |
| 4,189,385 | 2/1980 | Greenspan | 210/927 X |
| 4,268,393 | 5/1981 | Persidsky et al. | 210/516 |
| 4,322,298 | 3/1982 | Persidsky | 494/21 X |
| 4,416,778 | 11/1983 | Rogers | 210/927 X |

Primary Examiner—Benoit Castel
Assistant Examiner—W. Gary Jones
Attorney, Agent, or Firm—Cesari and McKenna

[57] ABSTRACT

Apparatus for separating or partitioning different density components of a liquid includes a liquid transfer pack composed of first and second flexible bags whose interiors are connected by tubing and a carrier for supporting the transfer pack. the carrier includes first and second sections defining first and second chambers for containing said first and second bags which sections can telescope between an extended condition wherein the volume of the second chamber is a maximum and a collapsed or retracted condition wherein the volume of the second chamber is a minimum. The two sections are biased toward their extended condition so that the first and second bags can be positioned in said chambers so that when the carrier and pack are spun at a selected high speed about an axis perpendicular to the carrier telescoping axis, the carrier sections will retract thereby maintaining the second bag in a collapsed condition in the second chamber minimum volume until the spinning slows to a selected lower speed. Whereupon, the carrier sections extend so that the second chamber assumes its maximum volume allowing the second bag to extend so that the densest components of a liquid in the first bag flow into the available volume in the second bag. Specific transfer pack and carrier constructions are also disclosed.

27 Claims, 7 Drawing Figures

APPARATUS FOR SEPARATING OR COLLECTING DIFFERENT DENSITY LIQUID COMPONENTS

This invention relates to the separation of liquid components according to their densities. It relates more especially to improved apparatus for effecting such separations and it has particular application to the partitioning and collecting of different blood components.

BACKGROUND OF THE INVENTION

The red blood cells or erythrocytes in donor blood have a certain life span. Actually, human blood contains more or less equal portions of red blood cells of ages between about 0 and 120 days. Thus, in any given sample, there is a certain percentage of younger blood cells or so-called neocytes and a certain percentage of older cells call gerocytes. Also, human blood contains a relatively large amount of iron, on the order of 108 mg/dl of red cells, the iron content being relatively uniform regardless of the average cell age of the blood sample. Therefore, it is desirable to transfuse patients with younger blood cells in order to minimize the number of required transfusions, thereby minimizing the amount of iron introduced into the patient's body. It has also been recognized that the older red cells in donor blood are more dense than the younger ones. Using this knowledge, attempts have been made to separate the red cells in a donor sample according to their densities so as to segregate the younger cells or neocytes from the older cells or gerocytes.

The usual technique for separating whole blood in accordance with the densities of the blood fractions is to place the blood sample in a container and spin the container about an axis perpendicular to the container axis at a high speed to subject the container contents to a centrifugal force on the order of 2,000 G. The force exerted on the blood sample causes the heaviest, most dense blood fractions such as the red cells to accumulate at the end of the container distal to the spin axis, while the less dense fractions, such as the blood plasma, accumulate at zones in the container progressively closer to the spin axis. Typical apparatus for effecting density separation of blood fractions by centrifuging are disclosed in the following U.S. Pat. Nos.: 3,064,647, Earl; 3,935,113, Ayres; 3,750,645, Bennet et al.: 3,945,928, Ayres; 3,800,947, Smith; 4,187,861, Heffernan; 3,887,464, Ayres; 4,189,385, Greenspan; 4,268,393, Persidsky et al.

Relatively recently, a new technique described in U.S. Pat. No. 4,416,778 owned by the assignee of the present application, has been developed for separating the components of a liquid, including blood, according to their densities. In that apparatus, the sample liquid is placed in a first chamber and centrifuged at a high speed so as to distribute the liquid components in that chamber along a density continuum. Following that high speed centrifuging step, the liquid components in the first chamber are partitioned by transferring to a second chamber only those components beyond a selected partition line in the density continuum established in the first chamber so that the components in the two chambers are separated by density and can be used independently.

The apparatus disclosed in that patent for separating the blood components comprises two flexible bags connected by a tube, with the bags being mounted to two coupling sections which are releasably connected together during the separation process. That patented apparatus also includes valve structure for controlling the flow of fluid between the two chambers during the separation process.

While that apparatus separates blood and other liquids by density precisely and effectively, it is not as easy to manufacture and use as might be desired, primarily because of the requirement to mechanically couple together the two flexible bags in which the liquid sample is separated. The coupling components also add to the overall cost of the apparatus. Also, special seals and/or gaskets must be provided between the bags and the coupling components to provide the required valving between the two bags. Furthermore, those seals must be able to withstand the very high fluid pressures developed when the apparatus is spun at the very high speeds required to develop the density gradient in the liquid sample.

SUMMARY OF THE INVENTION

Accordingly, the present invention aims to provide improved apparatus for separating a liquid sample by density.

Another object of the invention is to provide improved apparatus for collecting from a liquid sample fluid components thereof having a selected density range.

A further object of the invention is to provide such apparatus comprising a pair of connected-together flexible bags which does not require the mechanical coupling of the two bags.

Still another object of the invention is to provide apparatus of this general type which does not leak even when centrifuged at very high speeds.

Another object of the invention is to provide liquid separation apparatus of the type including two connected-together chambers which has a particularly effective valve structure for controlling flow of liquid between the two chambers.

Yet another object of the invention is to provide apparatus for partitioning a liquid by the density of its components which is easy to use by the average medical technician.

Still another object of the invention is to provide such apparatus which facilitates the selection of the partition line in the density continuum at which the liquid sample is to be separated.

Yet another object of the invention is to provide such apparatus which is especially suited to separating blood platelets from plasma or partitioning red blood cells according to their densities or ages.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, the present apparatus comprises a liquid transfer pack and a rigid reusable carrier for supporting the pack during centrifuging. The transfer pack comprises at least two flexible bags connected by a tube to form a completely enclosed fluid-tight system. One bag, denominated the upper bag, is relatively large and is used to contain the sample liquid whose components are to be separated by density. The other bag, herein the lower bag, is usually smaller than the upper bag and in its normal unflexed condition is more or less cylindrical in shape. Prior to use, air is removed from the lower bag so that it assumes a more or less flattened condition. Also, the tube connecting the bags is closed by a plug or stopper to prevent premature flow of liquid between the two bags.

The carrier component of the present apparatus comprises upper and lower sections which are telescopically or slidably connected for relative movement along the longitudinal axis of the carrier. The upper section defines an internal chamber for supporting the filled upper bag of the transfer pack. The lower section of the carrier is shaped to support the lower bag of the transfer pack in a second chamber below the bottom wall of the upper section. The two sections are shaped so that the upper section constitutes a piston which slides down into the lower section chamber and against the lower bag contained therein when the two sections telescope together. The carrier includes springs for biasing the two sections to their extended condition so that the upper section normally does not engage the bag contained in the lower section chamber.

To facilitate inserting the transfer pack into the carrier, the carrier is divided vertically into two parts which are hinged together so that the carrier can be opened more or less like a clamshell, exposing the interiors of the bag-supporting chambers defined by the two carrier sections.

To use the apparatus, the upper bag of the transfer pack is filled with the sample liquid which remains in the upper bag because the tubing connecting the two bags is plugged. The carrier is then opened and the transfer pack positioned in the carrier by placing the upper bag in the upper section of the carrier and the lower bag in the lower section thereof. Next, the carrier is closed and locked so that the bags are supported all around within the chambers defined by the two carrier sections. The carrier is then placed in a centrifuge and spun at a selected high speed about a spin axis perpendicular to the longitudinal axis of the carrier and located beyond the upper end of the carrier remote from the lower bag therein. As the speed increases, the two carrier sections telescope together due to the centrifugal force developed during spinning until the upper section presses against the bag in the lower section chamber. At that point, the plug which prevents fluid flow between the two bags is captured by the upper carrier section, but the plug remains in place blocking fluid flow between the two bags as long as the high speed spinning continues.

During the spin cycle, the components of the liquid in the upper bag stratify according to their densities so that a density continuum or gradient is formed along the length of the upper bag with the least dense liquid components being located proximal to the spin axis and the most dense liquid components being located distal to that axis adjacent to the closed tube leading to the second bag.

At the end of the spin cycle as the centrifuge slows down, springs in the carrier urge the two carrier sections apart to their extended condition. As the two sections move apart, the plug captured by the upper section is pulled out of the connecting tube, thereby establishing a fluid path between the two bags. As the carrier continues to spin at a relatively slow rate, the lower bag fills with the densest components of the sample liquid in the upper bag since those components are located at the bottom of the upper bag and are thus first to enter the connecting tube. The volume in the lower bag available to be filled by the liquid effluent from the upper bag determines the amount of liquid that flows from the upper bag and therefore the location of the partition line in the density continuum established in the liquid contained in the upper bag.

In other words, if only a relatively small volume of liquid flows from the upper to the lower bag after centrifuging, only the densest liquid components adjacent the bottom of the upper bag pass to the lower bag. On the other hand, if the lower bag has a larger volume, it will fill with liquid components from a higher elevation in the upper bag so that the contents of the lower bag will have a lesser average density. Thus, by properly selecting the available volume in the lower bag, the sample liquid can be partitioned along any line the density continuum established in the upper bag, with those components lying below the selected partition line being collected in the lower bag and the liquid components above that partition line remaining in the upper bag.

When the separation is completed and the centrifuge stops spinning, the carrier is removed from the centrifuge and opened, the tube between the two bags is clamped and the two bags are separated, thereby yielding a dense liquid component fraction in the lower bag and a less dense component fraction in the upper bag.

The present apparatus is particularly suitable for separating or collecting different density components of human or animal blood. For example, it can be used to separate blood platelets from plasma and to separate the more dense older red blood cells or gerocytes from the less dense younger cells or neocytes to achieve all of the benefits discussed in the aforesaid U.S. Pat. No. 4,416,778. The apparatus is also reliable and easy to use, the sample liquid that is subjected to the separation process remaining in a completely sterile environment within the transfer pack during all stages of the process. The apparatus also produces liquid separations or partitions that are accurate and repeatable. Consequently, it should find wide application, particularly in the medical field where fast, accurate and reliable liquid separations are needed on a day-to-day basis.

BRIEF DESCRIPTION OF THE DRAWINGS

For a fuller understanding of the nature and objects of the invention, reference should be had to the following detailed description, taken in connection with the accompanying drawings, in which.

DESCRIPTION OF THE PREFERRED EMBODIMENT

Figure 1:
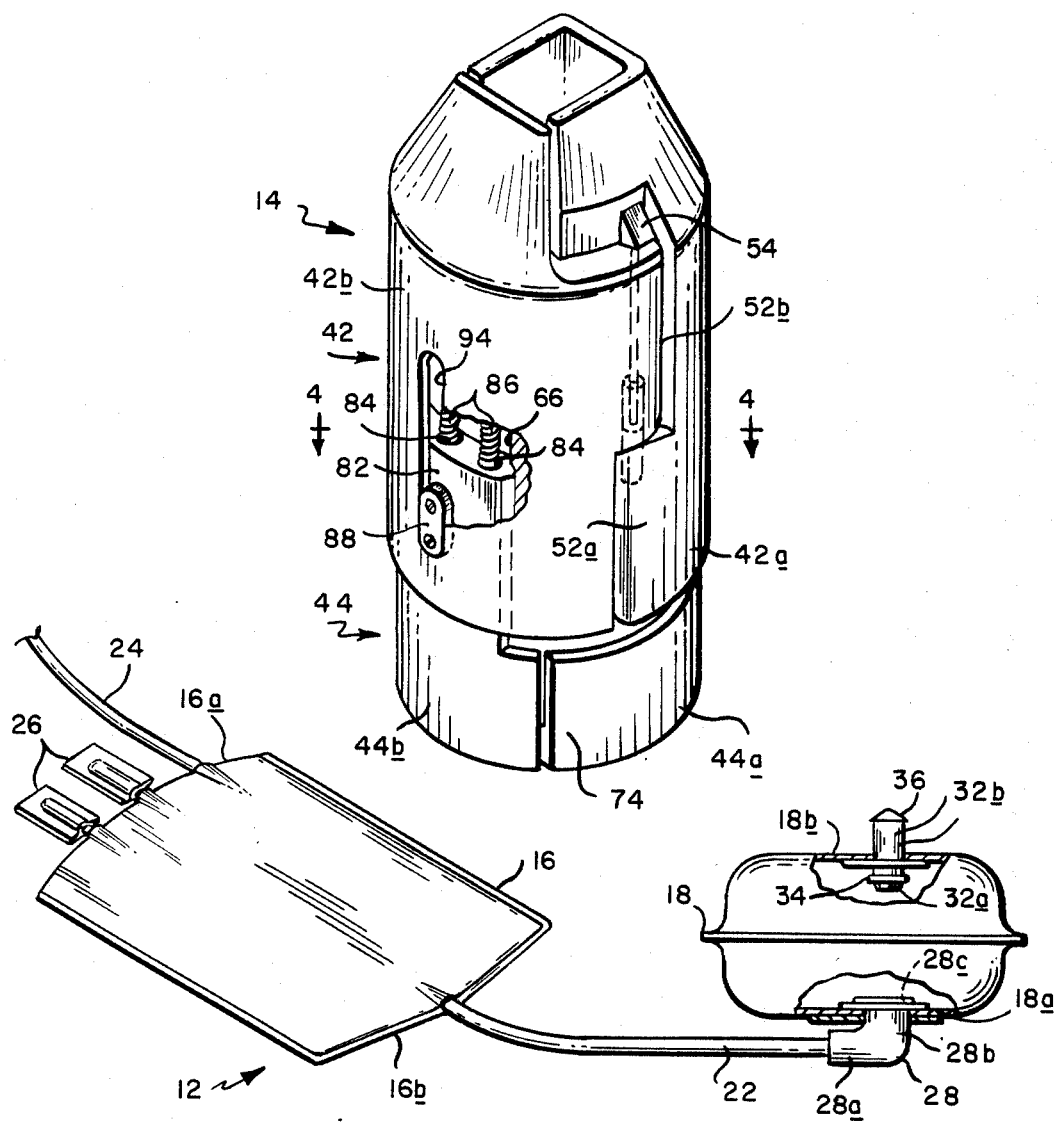
FIG. 1 is a perspective view showing apparatus including a transfer pack and carrier therefore for separating or collecting components of a liquid in a selected density range.
Figure 2:
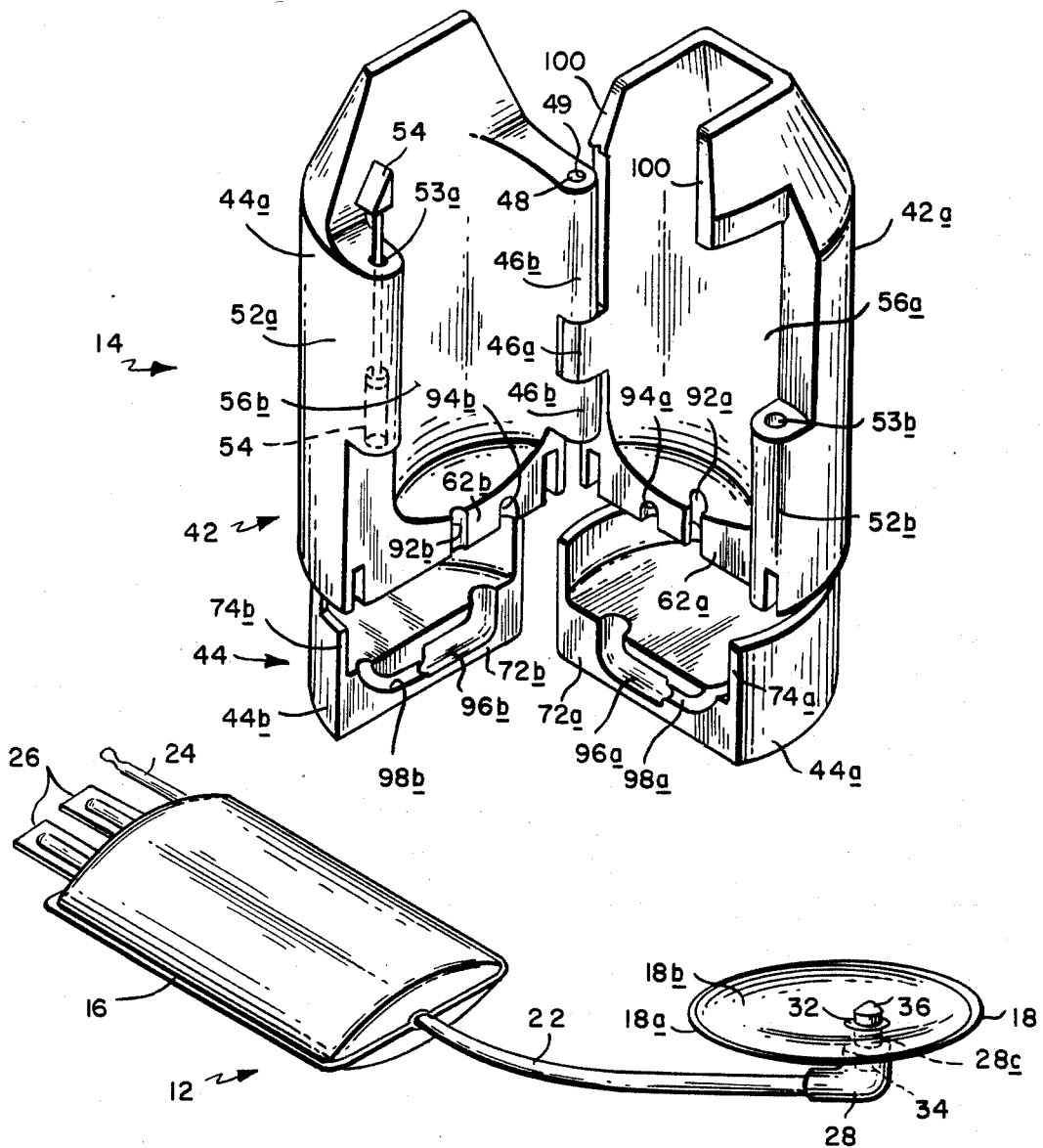
FIG. 2 is a similar view showing the transfer pack and carrier components of the apparatus prepared for use.

Referring to FIGS. 1 and 2 of the drawings, the apparatus comprises a liquid transfer pack indicated generally at 12 and a carrier therefor shown generally at 14.

The transfer pack 12 is a two-bag pack of a type that could be used to separate components of animal or human blood. For purposes of discussion, we will describe the invention in this context. It should be understood, however, that the disclosed apparatus is just as capable of separating or collecting different density components of other sample liquids.

Transfer pack 12 comprises a relaively large upper bag 16 and a smaller lower bag 18, the interiors of the bags being connected by length of tubing 22. Bag 16 is made of a flexible plastic material and, in many respects, is similar to a standard blood bag described, for example, in U.S. Pat. No. 3,064,647 used for blood transfusion and blood component separation. It is fitted with an inlet tube 24 and removably sealed access ports 26 incorporated into the seam 16a at the upper end of the bag and one end of tube 22 is welded into the seam 16b at the lower end of the bag. When empty, bag 16 is more or less flat as shown in FIG. 1. However when the bag is filled with liquid and distended, at least its lower segment assumes a flattened cylindrical shape. See FIG. 5A.

Bag 18 is also flexible and when distended has the general shape of a cylinder or flattened sphere. The lower end of tube 22 is connected to one arm 28a of an elbow fitting 28. The other arm 28b of that fitting is sealed into an opening formed in the lower wall 18a of bag 18 so that the open end 28c of fitting arm 28b lies inside the bag. Preferably, the wall 18a around the fitting is reinforced as shown. As best seen in FIG. 1, the fitting 28 is not connected to bag wall 18a at the center of that wall, but is displaced radially to one side of the bag for reasons that will become apparent later.

Figure 5B:
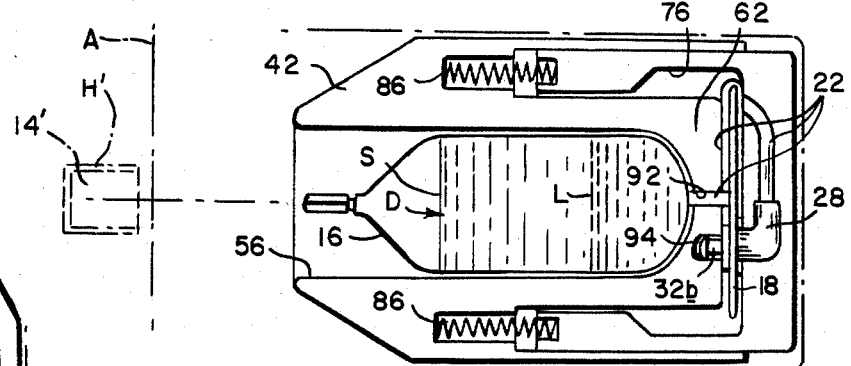
FIGS. 5A to 5C are longitudinal sectional views illustrating the operation of the apparatus.

Positioned directly opposite the fitting end 28c is a plug 32 which is reinforcingly sealed into an opening formed in the upper wall 18b of bag 18 so that a lower section 32a of the plug extends inside bag 18, while an upper section 32b thereof projects above the bag. Plug 32 is generally cylindrical in shape but its lower section 32a is formed with an integral circumferential bead 34 whose diameter is the same or slightly larger than the inside diameter of the fitting end 28c so that the plug section 32a can be inserted into the fitting end 28c with the bead 34 thereon forming a fluid-tight seal with the inside wall of the fitting as best seen in FIGS. 2 and 5B. The exposed upper section 32b of the plug functions more or less as a gripping handle and its free end is formed with a radial flange or barb 36. Preferably, when the transfer pack 12 is delivered from the manufacturer, bag 18 is evacuated so that it assumes a flat concave shape shown in FIG. 2 and plug 32 is seated in the fitting end 28c so that the entrance to bag 18 through tube 22 is sealed shut as shown in FIG. 2.

Still referring to FIGS. 1 and 2, carrier 14 is a generally cylindrical container molded or machined of a very strong impact-resistant material such as urethane or polycarbonate. The carrier comprises an upper section 42 and a slightly smaller diameter lower section 44 which is telescopically received into the lower end of section 42 so that the two sections can slide between an extended position shown in FIGS. 1 and 5A and a collapsed position shown in FIG. 5B. Carrier 14 is actually divided vertically more or less down the middle so that its upper section 42 is separated into two parts, 42a and 42b, while lower section 44 is separated into two parts, 44a and 44b as shown in FIG. 2. Interfitting gudgeons 46a and 46b are formed at the corresponding rear edges of carrier section parts 42a and 42b and the gudgeons are swingably or hingedly connected together by an appropriate pin or pintel 48 (FIG. 2) extending down through registering vertical openings 49 in the interfitting gudgeons 46a and 46b. The two parts of carrier 14 can thus swing more or less like a clamshell between an open position illustrated in FIG. 2 wherein clear access is had to the interiors of carrier sections 44a and 44b and a closed position shown in FIG. 1 wherein the interiors of the two carrier sections are completely closed and the carrier as a whole assumes the general cylindrical outer shape illustrated in that figure.

Preferably, means are provided for locking the carrier in its closed position. In the illustrated embodiment, the corresponding front edges of the carrier section parts 42a and 42b are notched and have tabs or teeth 52a and 52b which are vertically offset so that, when the carrier is closed, those teeth interfit as shown in FIG. 1. A vertical passage 53a extends through tab 52b for slidably receiving a locking pin 54. When the carrier is in its closed position, hole 53a registers with a vertical hole in tab 52a so that pin 54 slides down into hole 53b to lock carrier section 42, and thus the carrier as a whole, in its closed position shown in FIG. 1.

Figure 4:
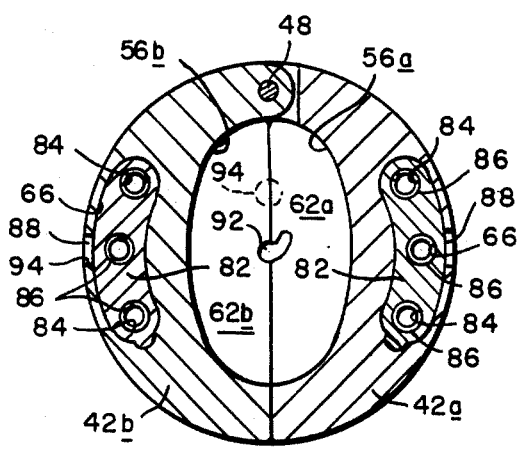
FIG. 4 is a sectional view along line 4—4 of FIG. 1.
Figure 5A:
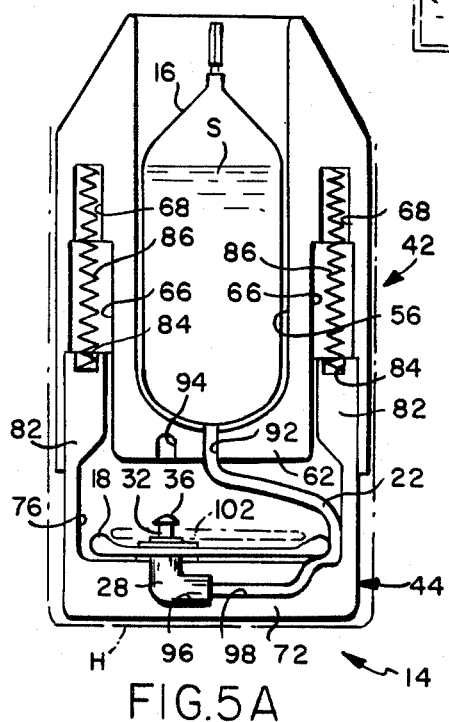

Referring now to FIGS. 2, 4 and 5A, the inside walls 56a and 56b of the carrier section parts 42a and 42b have more or less the curvature of a flattened cylinder so that, when the carrier is closed, the two carrier section parts define a flattened cylindrical cavity or chamber 56 (FIG. 5A) inside carrier section 42. The upper end of that cavity is open. However, the lower end of the cavity is closed by bottom wall parts 62a and 62b of carrier section parts 42a and 42b respectively. When the carrier is closed, those two wall parts 62a and 62b come together to form a full bottom wall 62 (FIG. 5A) for the chamber 56 as a whole.

As best seen in FIGS. 1, 4 and 5A, a relatively deep slot 66 extends up into the side wall of each upper section part 42a and 42b. Each such slot is relatively wide, cylindrical in cross section and extends slightly more than half the length of carrier section 42. Also, a plurality of axial holes 68 (FIG. 5A) are drilled into the floor of each slot 66. Slots 66 are arranged to slidably receive the lower section halves 44a and 44b. More particularly and as shown in FIGS. 2 and 5A, carrier section 44 is shaped more or less as a cup with an outer diameter slightly less than the outer diameter of section 42. It has a bottom wall 72 which is divided vertically so that one part 72a is formed in carrier section part 44a and the other part 72b is formed in carrier section part 44b.

The circular section defined by wall part 72a is larger than that defined by wall part 72b so that the former forms a relatively large accessible shelf when the carrier is in its open position shown in FIG. 2. Also, carrier section parts 44a and 44b are formed with curved peripheral side walls 74a and 74b which extend up from their respective bottom wall parts 72a and 72b. When the carrier is closed, those walls come together to provide a continuous circular side wall 74 (FIG. 1) all around carrier section 44 and help form within that section a relatively shallow cylindrical chamber 76 as shown in FIG. 5A, that chamber being considerably shorter, but more or less of the same diameter as the upper chamber 56 in carrier section 42.

As best seen in FIGS. 1, 4 and 5A, carrier section parts 44a and 44b also include upwardly extending, arcuate-in-cross-section tongues 82 which are shaped and dimensioned to be slidably received in the slots 66 in carrier section parts 42a and 42b. Lengthwise holes 84 are drilled in tongues 82 so that, when the tongues are received in slots 66, those holes 84 lie directly opposite the corresponding holes 68 formed in those slots.

Coil compression springs 86 are positioned with their opposite ends in corresponding holes 68 and 84 of each carrier part so that those springs tend to bias the two slidably connected or telescoping carrier sections 42 and 44 apart longitudinally. The lengthwise sliding movement of section 44 relative to section 42 is limited by glides or sliders 88 projecting laterally from tongues 82 and which slide along vertical slots 94 formed in carrier section parts 42a and 42b. The length of slots 94 is such that the carrier sections 42a and 42b can move between an extended condition illustrated in FIGS. 1 and 5A and a retracted condition illustrated in FIG. 5B. In the former, the bottom wall 62 of carrier section 42 is spaced appreciably from the bottom wall 72 of carrier section 74 so that the lower chamber 76 has an appreciable height dimension. In the latter condition, the two walls 62 and 72 lie close together so that the height of the lower chamber 76 in carrier section 44 is very small or almost nonexistent.

In other words, when the carrier sections move relatively between their extended and collapsed or retracted condition, the upper section bottom wall 62 functions more or less as a piston which moves up and down in the lower section chamber 76. As mentioned previously, the two sections are normally maintained in their extended condition shown in FIG. 5A by the compression springs 86. Thus, when carrier 14 is closed as in FIGS. 1 and 5A, it normally defines an upper fixed volume chamber 56 and a lower variable volume chamber 76 whose volume is determined by the degree of extension of the two carrier sections 42 and 44.

As best seen in FIGS. 2, 4 and 5A, a vertical axial passage 92 is formed in upper carrier section bottom wall 62 which connects the carrier chambers 56 and 76 and is sized to snugly receive tube 22. Passage 92 is located right at the counterfacing surfaces of the carrier section bottom wall parts 62a and 62b so that one half of that passage is defined by a vertical groove 92a in wall part 62a and the other half is defined by a vertical groove 92b in wall part 62b. Consequently, when the carrier is open as shown in FIG. 2, there is sideways access into passage 92. Also formed in the counterfacing surfaces of bottom wall parts 62a and 62b between grooves 92 and hinge pin 48 are a pair of arcuate upwardly extending slots or grooves 94a and 94b which, when the carrier is closed, cooperate to define a short cylindrical hole 94 (FIG. 5A) that extends parallel to hinge pin 48 and opens into the lower chamber 76 at a location offset toward the hinge pin from the longitudinal axis of the carrier. Hole 94 is sized to tightly receive the plug section 32b on bag 18 of the transfer pack. See FIG. 5B.

Further as best seen in FIGS. 2 and 5A, L-shaped grooves 96a and 96b are formed in the bottom wall parts 72a and 72b of carrier section 44 directly below the aforementioned grooves 94a and 94b. When the carrier is closed as shown in FIG. 1, the grooves 96 come together to define an L-shaped cavity 96 (FIG. 5A) in the carrier section bottom wall 72 which is dimensioned to receive the L-shaped elbow fitting 28 on bag 18 of the transfer pack. Further, additional grooving 98a and 98b is provided in the bottom wall parts 72a and 72b which, when the carrier is closed, define a channel 98 (FIG. 5A) which extends horizontally through the lower section bottom wall 72 and then gradually upward where it communicates with the lower chamber 76 near the outer wall of that chamber. The channel 98 is sized to receive the tube 22 which connects the two bags 16 and 18 of the transfer pack illustrated in FIG. 1.

To use the present apparatus, the bag 16 of the transfer pack is filled through inlet tube 24 with the liquid sample S to be processed, after which that tube is sealed as shown in FIG. 2. As mentioned previously, when the transfer pack 12 is delivered by the manufacturer, its bag 18 is preferably evacuated and plug 32 is plugged into the elbow fitting 28 thereby closing tube 22 so that there is no liquid flow from bag 16 and no air in bag 18 that could affect the volume of that bag available for the effluent from bag 16.

Figure 3:
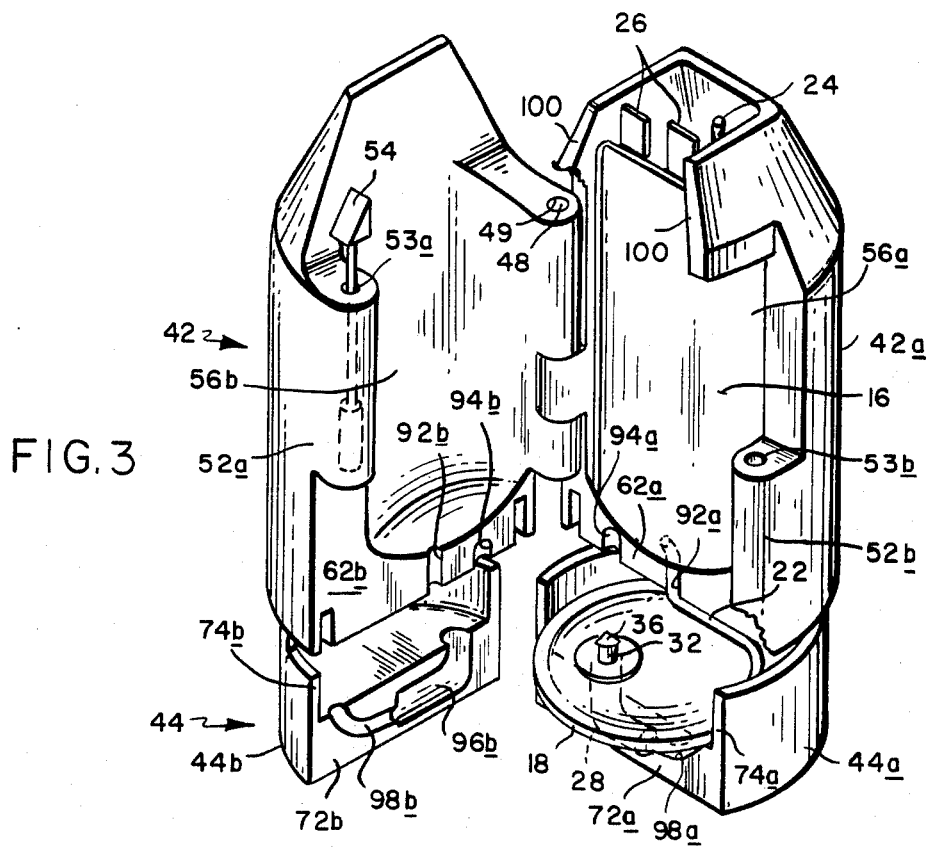
FIG. 3 is another perspective view illustrating the transfer pack positioned inside the carrier.

The carrier component 14 of the apparatus is then opened and bag 16 of the transfer pack 12 is laid into the carrier upper section part 42a as shown in FIG. 3. A pair of tongues 100 formed at the upper end of that part help to fold the side edges of bag 16 so that the bag does not interfere with the closing of the carrier. The flattened evacuated bag 18 is then laid into the lower carrier section part 44a so that its elbow fitting 28 seats in groove 96a in the bottom wall of part 62a. Also, tube 22 is seated in groove 98a in that same wall and wound around bag 18 to the back of carrier section part 44a. Preferbly, fitting 28 and tube 22 have snug fits in their respective grooves 96a and 98a so that they more or less snap into place and remain there. The tubing extending toward bag 16 is laid on top of bag 18 underneath the bottom wall part 62a of the upper carrier section, with the portion of that tubing adjacent bag 16 being placed in the vertical groove 92a. That groove 92a is specially shaped as shown so that the tube snaps into the groove and is held there. Consequently, it is quite easy to load the transfer pack 12 into the carrier, even with one hand. Then the carrier is closed, with the operator taking pains to ensure that the overhanging portion of bag 18 rests properly on the left-hand part 44a of the lower section 44. After the locking pin 54 engages in hole 53b, the carrier is locked in its closed position capturing bag 16 in upper chamber 56 and enclosing bag 18 at the bottom of lower chamber 76, with tube 22 extending through passage 92 and plug 32 located directly below the hole 94 in the upper section bottom wall 62 as shown in FIG. 5A.

Next, the carrier is placed in a conventional centrifuge swing head indicated in dotted lines at H in FIG. 5A. It should be noted that at this stage, the liquid sample S is still contained in bag 16 because tube 22 is still blocked by plug 32. When the centrifuge is turned on, the swinghead H and the carrier 14 therein swing out sideways and rotate about an axis A spaced from the upper carrier section 42 and distal to bag 18 of the transfer pack as shown in FIG. 5B. The centrifuge is accelerated up to a very high speed, so as to subject the carrier and its contents to a high centrifugal force, e.g. 2,000 G. That force thrusts the carrier radially outward in the centrifuge head H so that the head applies a centripetal force to carrier section 44 which causes that section to telescope or retract into section 42 in opposition to the bias provided by springs 86. The lower wall 62 of section 42 thus advances as a piston into the carrier lower chamber 76 until it engages and presses against the bag 18 with the plug 32 on that bag being wedged into hole 94 as shown in FIG. 5B. During this high-speed spinning, then, tube 22 remains blocked by plug 32. Since the carrier is locked closed, its two parts cannot open to prevent the carrier section 42 from sliding down into the head H as section 44 retracts. Preferably also, the centrifuge is provided with a counterbalancing centrifuge head H' containing a dummy carrier 14' as indicated in dotted lines in FIG. 5B, because of the moving center of mass of carrier 14. In other words, as carrier section 44 retracts, the centrifuge would become unbalanced and could shut off automatically unless counterbalanced by a similar carrier 14'.

It is important to note that the lower portion of upper bag 16, including its lower seam 16b at the mouth of tube 22, is snugly supported all around by the upper carrier section walls 56a, 56b, 62a and 62b, while the segment of tube 22 is encircled and supported by the walls of passage 92. Still further, the segment of tube 22 that was positioned between bag 18 and the upper section bottom wall 62 as described above is pressed flat between the walls 62 and 72. Therefore, neither bag 16 nor those tubing segments is subjected to excessive stress despite the very high G forces thrusting the liquid against the bottom portion of bag 16 and those tubing segments. This pressing flat of the supported tube segment just below bag 16 prevents liquid flow further along the tube 22 so that the unsupported downstream segment of the tube, fitting 28 and bag 18 and the seams or joints between them are not exposed to the rupturing effects of the liquid being centrifuged. Resultantly, there is no leakage of liquid from the transfer pack 12. It should be noted also that the upper section 42 or, more particularly, its bottom wall 62 advances as a piston into chamber 76 and bottoms out or seats flush against the bottom wall 72 of the lower section 44, which is, in turn, snugly supported by the centrifuge head. Therefore, the carrier parts are not overly stressed despite the high G forces acting on the carrier as a whole.

The high speed spinning step is continued for a length of time depending upon the nature of the liquid in bag 16. When separating blood neocytes from gerocytes, for example, the carrier and its contents are spun for about fifteen minutes. During this time, the components of the liquid sample S in bag 16 separate according to their densities with the most dense components tending to accumulate at the bottom of bag 16 remote from the spin axis A and the least dense components accumulating at the top of the bag proximal to that axis, intermediate densities occupying the positions in the bag 16 between those two extremes. Resultantly, a density gradient or continuum is established in the bag 16 contents as indicated at D in FIG. 5B.

Figure 5C:
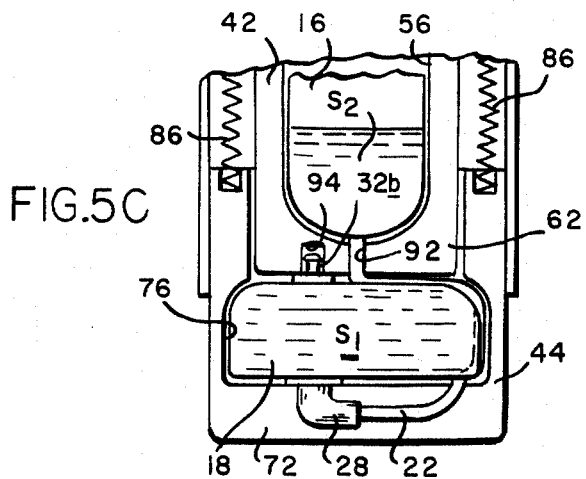

After the carrier and it contents have been spun for the requisite length of time, the centrifuge is turned off. As the centrifuge slows down, the centripetal force acting on the carrier decreases gradually so that the compression springs 86 gradually return carrier section 44 to its extended position. Because the plug section 32b is captured in hole 94, as the bottom wall 62 of the upper section 42 moves away from the lower wall 72 of the lower section 44, the plug 32 is pulled out of the elbow fitting 28 so that tube 22 is no longer blocked. Also, the upper section bottom wall 62 no longer presses against tube 22 so that the liquid in bag 16 can flow from bag 16 through tube 22 to bag 18 as shown in FIG. 5C. At this point, the centrifuge may still be spinning at a relatively low speed so that the force acting on the carrier is only about 250 to 400 G. This continued spinning at the lower rate of speed helps to move the liquid gently from bag 16 to bag 18.

The flow of liquid into bag 18 continues until a fraction $S_1$ of the liquid sample S fills the available volume in that bag, leaving a remaining sample fraction $S_2$ in bag 16. Preferably, the bag 16 is oversized so that the liquid flow is controlled solely by the available volume in bag 18. The size of that available volume therefore determines the location or line L (FIG. 5B) in the density continuum D established in the liquid sample S in bag 16 where the density separation or partition is to take place. The smaller the volume of the fraction $S_1$ flowed into bag 18, the further down in the density continuum is the separation or partition and the greater the average density of the liquid fractin $S_1$ accumulated in bag 18. Conversely, if bag 18 has a larger volume, more liquid can flow from bag 16 so that the partition or separation of the liquid sample in that bag occurs further up in the density continuum D established in the bag 16 contents. Thus, in the case of blood cell separations, for example, as the available volume of bag 18 increases, the average density and age of the blood cell fraction $S_2$ remaining in bag 16 after centrifugation decreases, and vice versa.

After the centrifuge stops, carrier 14 is opened by releasing the locking pin 54. The opening of the carrier 14 automatically releases plug 32 from its split hole 92 so that bag 18 can be removed easily from the carrier. Then, without overly disturbing the two bags, tube 22 is clamped, preferably close to bag 16, thereby isolating the contents of the two bags, following which the tube 22 is sealed and severed to separate bags 16 and 18, their contents, now consisting of the fractions $S_1$ and $S_2$ having two distinct component density ranges from the original liquid sample S.

The effective volume of bag 18 which determines the amount of liquid that will flow into that bag from bag 16 when tube 22 is unblocked after the high speed centrifugation step (and thus the location of partition line L) is determined primarily by the maximum volume of the lower chamber 76 in carrier section 44, i.e. when the carrier is fully extended as shown in FIG. 5C. That volume can be varied by varying the locations of the lower ends of the vertical slots 94 in carrier section 42 or by changing the lengths or positions of the glides 92. Another way of controlling the effective volume of bag 18 without changing the carrier 14 at all is to place slit filler rings on top of bag 18 in chamber 76 as indicated in dotted lines at 102 in FIG. 5A. Each ring 102 is made of foam rubber or other resilient material so that when the carrier is spun at high speed and collapses as shown in FIG. 5B, the rings 102 are compressed between bag 18 and the upper carrier section bottom wall 66 so that the rings do not prevent the plug section 32b from being wedged into hole 94. However, at the end of the spin cycle when the centrifuge slows down and carrier 14 extends, the rings 102 have sufficient resilience to return to their full thickness. Thus, the rings will occupy a fixed portion of the volume in chamber 76, thereby limiting the extent to which the bag 18 can unfold or extend. That, of course, limits the available volume inside that bag into which the liquid from bag 16 can flow. Thus, by properly selecting the thickness or number of rings 102, one can select the particular line along the density continuum D established in the liquid sample S in bag 16 at which the separation or partition will take place.

It will be appreciated from the foregoing that, since the transfer pack 12 consists solely of the connected-together flexible bags and tubing, it can be made relatively easily and inexpensively and delivered in a septic or sterile condition inside an appropriate sealed envelope. Once the bag 16 is filled with the liquid sample S and the inlet tube 24 is closed, the transfer pack constitutes a closed system whose contents can be kept free of contaminants. Also, once the dies or molds for forming the carrier 14 are made, the carrier can be reproduced in quantity at a reasonable cost. Furthermore, since the carrier is made of a strong, rugged, impact-resistant plastic material that can withstand autoclaving temperatures, it can be reused and thus has a relatively long life expectancy. Finally, the apparatus is easy for the operator to use and it can produce separations which are reliable and repeatable in a relatively short period of time. Therefore, the apparatus should find wide application in laboratories, hospitals and clinics whenever separations of liquids according to density are required on a regular basis.

It will thus be seen that the objects set forth above, among those made apparent from the preceding description, are efficiently attained, and, since certain changes may be made in the above construction without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention herein described.

What is claimed as new and desired to be secured by Letters Patent of the United States is:

1. Apparatus for separating or collecting different density components of a liquid comprising
   A. a liquid transfer pack including
      (1) a first flexible bag;
      (2) a second flexible bag having an available volume smaller than that of the first bag; and
      (3) a flexible tube connecting the interiors of the two bags to form a substantially closed system; and
   B. a carrier, said carrier including
      (1) a first section defining a first chamber for containing the first bag, said first section including a bottom wall;
      (2) a second section defining with said first section wall a second variable volume chamber for containing the second bag, said section being dimensioned to fit one inside the other so that they are telescopically connected together whereby the two sections can slide axially relative to one another between an extended condition wherein said bottom wall does not project appreciably into the second section and the volume of the second chamber is a maximum and a retracted condition wherein said bottom wall does project into the second section and the volume of the second chamber is a minimum;
      (3) a passage extending between said chambers; and
      (4) means for biasing the carrier sections toward said extended condition so that the first and second bags can be positioned in the first and second chambers respectively with said tube extending between said chambers through said passage whereby, when the carrier and said pack therein are spun at a selected high speed about an axis generally perpendicular to the carrier telescoping axis, said carrier sections will retract in opposition to said biasing means thereby maintaining the second bag in a collapsed condition in said second chamber minimum volume until said spinning slows to a selected lower speed whereupon said carrier sections will extend to said extended condition under the bias of said biasing means to permit said second bag to assume an uncollapsed condition in said second chamber maximum volume.

2. The apparatus defined in claim 1
   A. wherein said carrier is divided parallel to said telescoping axis so that said first and second sections are each composed of a pair of section parts; and
   B. further including means for hingedly connecting together at least one pair of section parts so that the carrier can be opened to permit said transfer pack to be loaded sideways into said chambers.

3. The apparatus defined in claim 2 and further including means for releasably locking said at least one section pair.

4. The apparatus defined in claim 1 and further including means for blocking fluid flow between said bags until said carrier and the pack therein are first spun at said selected high speed and then slowed to said selected lower speed.

5. The apparatus defined in claim 4 wherein said blocking means comprise
   A. plug means mounted in a wall of said second bag and engageable in the tube entrance into said second bag; and
   B. means on said carrier for
      (1) engaging said plug means when said carrier sections move from their extended to their retracted condition; and
      (2) pulling said plug means away from said tube entrance when said carrier sections move from their retracted to their extended condition.

6. The apparatus defined in claim 5
   A. wherein said plug means include a first plug section inside the second bag and a second plug section extending outside the second bag; and
   B. said engaging and pulling means comprise means on said carrier for gripping said second plug section when said carrier sections telescope to said retracted condition.

7. The apparatus defined in claim 6 wherein
   A. said first carrier section bottom wall separates said chambers;
   B. said passage is located in said bottom wall; and
   C. said gripping means comprise a hole in said bottom wall
      (1) which opens into said second chamber; and
      (2) which snugly receives the second plug section on said second bag positioned in said second chamber when said sections telescope to said retracted condition.

8. The apparatus defined in claim 7 wherein
   A. said carrier is composed of separate parts hingedly connected together along a line parallel to said telescoping axis so that said carrier can be opened to permit said transfer pack to be loaded sideways into said chambers;
   B. said bottom wall is composed of two mating wall parts contained in said separate carrier parts;
   C. said passage is formed by two registering grooves in the counterfacing surfaces of said bottom wall parts; and
   D. said hole is formed by two registering slots in said counterfacing surfaces of said bottom wall parts so that, when said carrier is opened, a second plug section received in said hole is automatically released from said hole.

9. The apparatus defined in claim 4 wherein said blocking means comprise means in said carrier for pressing against said tube when said carrier sections are in said retracted condition.

10. The apparatus defined in claim 9 wherein said pressing means comprise a wall of said first carrier section which separates said two chambers.

11. Apparatus for separating or collecting different density components of a liquid comprising
   A. a first flexible bag;
   B. means permitting introduction of a liquid into said first bag;
   C. a second collapsible flexible bag having an available volume smaller than that of the first bag;
   D. a flexible tube connecting the interiors of the two bags to form a substantially closed system;
   E. plug means
      (1) positioned inside said second bag; and
      (2) pluggable into the entrance of said tube into said second bag when said second bag is collapsed so as to prevent fluid flow between said bags; and
   F. gripping means attached to said plug means and accessible from outside the second bag to enable the plug means to be unplugged from said tube entrance when said second bag is extended from its collapsed condition so that fluid can flow between said bags.

12. The apparatus defined in claim 11 wherein
   A. said plug means
      (1) is mounted in a wall of said second bag opposite said tube entrance;
      (2) includes a first section extending from said bag wall toward said tube entrance; and
   B. said gripping means comprises a second plug section extending from said bag wall outside said second bag.

13. The apparatus defined in claim 12 wherein
   A. said first plug section includes sealing means thereon for sealingly engaging in said tube entrance; and
   B. the second plug section includes means thereon for facilitating the grasping of said second plug section.

14. The apparatus defined in claim 11 wherein said second bag has a generally circular cross section.

15. The apparatus defined in claim 11 wherein said plug means and said tube entrance are similarly offset laterally from the center line of said second bag.

16. The apparatus defined in claim 11 wherein said tube entrance into said second bag is formed by a rigid tube fitting sealed into wall of said second bag.

17. The apparatus defined in claim 11 and further including a carrier
   A. having a first chamber for containing said first bag;
   B. having a second, variable volume chamber for containing said second bag; and
   C. arranged to support said bags for spinning at a selected high speed in a centrifuge.

18. The apparatus defined in claim 17 wherein said second chamber assumes its minimum volume when said container is spun in the centrifuge at said high speed so that said second bag is maintained in a collapsed condition in said second chamber so long as said high speed spinning continues.

19. The apparatus defined in claim 18 wherein said carrier includes interior walls that provide close support for said bags and said tube so long as said high speed spinning continues so that said bags and tube are not overly stressed during said spinning.

20. Apparatus for separating or collecting different density components of a liquid comprising
   A. a first carrier section defining a first chamber for containing a first bag, said first section including a bottom wall;
   B. a second carrier section defining with said bottom wall a second variable volume chamber for containing a second bag;
   C. means for connecting said sections together so, that they can slide telescopically along an axis one inside the other between an extended condition wherein said first section wall does not project appreciably inside the second section and the volume of the second chamber is a maximum and a retracted condition wherein said bottom wall does project into the second section and the volume of said second chamber is a minimum;
   D. means defining a passage extending between said chambers for receiving a tube connecting bags contained in said chambers; and
   E. means for biasing said carrier sections toward their extended condition.

21. The apparatus defined in claim 20
   A. wherein said carrier is divided parallel to said telescoping axis so that said first and second sections are each composed of a pair of section parts; and
   B. further including means for hingedly connecting together at least one pair of said section parts so that the carrier can be opened to provide side access into said chambers.

22. The apparatus defined in claim 20 and further including means on one of said carrier sections
   A. exposed to said second chamber;
   B. which grips a portion of a second bag contained in said second chamber when said sections telescope to said retracted condition; and
   C. which pull said second bag portion to extend said second bag when said carrier sections return to their extended condition.

23. The apparatus defined in claim 22 wherein
   A. said first carrier section includes a bottom wall separating said chambers;
   B. said passage is located in said bottom wall; and
   C. said gripping means comprise a hole in said bottom wall opening into said second chamber and which snugly receives said portion of a second bag contained in said second chamber.

24. The apparatus defined in claim 23 wherein
   A. said carrier is divided parallel to said telescoping axis so that
      (1) said first and second sections are each composed of a pair of section parts; and
      (2) said bottom wall is composed of two parts contained in said second section parts so that said carrier sections can be opened to provide access into said chambers;
   B. said passage is formed by two registering grooves in the counterfacing surfaces of said bottom wall parts; and
   C. said hole is formed by two registering slots in said counterfacing surfaces of said bottom wall parts.

25. The apparatus defined in claim 24 and further including means for releasably locking together at least one pair of carrier section parts so that said carrier sections cannot be opened.

26. The apparatus defined in claim 24 wherein, when the carrier sections are closed and telescope to said retracted condition, said bottom wall parts function as a single piston which advances into said second chamber to reduce its volume to said minimum volume.

27. The apparatus defined in claim 23 wherein

A. said second section includes a bottom wall opposite said first section bottom wall; and
B. said upper section bottom wall can advance as a piston into said second chamber when said sections telescope to said retracted condition until said bottom walls make substantially flush contact whereby said apparatus is able to withstand high G forces when spun about an axis penpendicular to said telescoping axis.

* * * * *